United States Patent
Heep et al.

(10) Patent No.: US 11,617,792 B2
(45) Date of Patent: Apr. 4, 2023

(54) LIQUID COMPOSITION CONTAINING PRADOFLOXACIN

(71) Applicant: Bayer Animal Health GmbH, Leverkusen (DE)

(72) Inventors: Iris Heep, Cologne (DE); Patrick Billian, Brieselang (DE)

(73) Assignee: Bayer Animal Health GmbH, Leverkusen (DE)

( * ) Notice: Subject to any disclaimer, the term of this patent is extended or adjusted under 35 U.S.C. 154(b) by 408 days.

(21) Appl. No.: 16/998,390

(22) Filed: Aug. 20, 2020

(65) Prior Publication Data

US 2020/0376126 A1 Dec. 3, 2020

Related U.S. Application Data

(62) Division of application No. 16/484,670, filed as application No. PCT/EP2018/053176 on Feb. 8, 2018, now Pat. No. 10,780,168.

(30) Foreign Application Priority Data

Feb. 13, 2017 (EP) .................... 17155885

(51) Int. Cl.
| | |
|---|---|
| *A61K 47/20* | (2006.01) |
| *A61K 9/00* | (2006.01) |
| *A61K 9/08* | (2006.01) |
| *A61K 31/4709* | (2006.01) |
| *A61K 47/12* | (2006.01) |
| *A61K 47/26* | (2006.01) |

(52) U.S. Cl.
CPC ............ *A61K 47/20* (2013.01); *A61K 9/0019* (2013.01); *A61K 9/08* (2013.01); *A61K 31/4709* (2013.01); *A61K 47/12* (2013.01); *A61K 47/26* (2013.01)

(58) Field of Classification Search
CPC ...................................... A61K 47/12
See application file for complete search history.

(56) References Cited

U.S. PATENT DOCUMENTS

| | | |
|---|---|---|
| 6,278,013 B1 | 8/2001 | Bartel et al. |
| 6,323,213 B1 | 11/2001 | Bartel et al. |
| 6,436,955 B1 | 8/2002 | Himmler et al. |
| 6,492,391 B1 | 12/2002 | Himmler et al. |
| 6,664,268 B1 | 12/2003 | Himmler et al. |
| 6,995,170 B1 | 2/2006 | Himmler et al. |
| 7,977,484 B2 | 7/2011 | Rast et al. |
| 2008/0125458 A1 | 5/2008 | Rast et al. |
| 2015/0080387 A1 | 3/2015 | Heep et al. |

FOREIGN PATENT DOCUMENTS

| | | |
|---|---|---|
| AU | 2012202013 A1 | 5/2012 |
| JP | 2004/067516 A | 3/2004 |
| JP | 2007/077061 A | 3/2007 |
| JP | 2009/544665 A | 12/2009 |
| WO | 9731001 A1 | 8/1997 |
| WO | 9929322 A1 | 6/1999 |
| WO | 0031075 A1 | 6/2000 |
| WO | 0031076 A1 | 6/2000 |
| WO | 0031077 A1 | 6/2000 |
| WO | 0052010 A1 | 9/2000 |
| WO | 2005097789 A1 | 10/2005 |
| WO | 2005/107759 | 11/2005 |
| WO | 2016/036308 A1 | 3/2016 |
| WO | 2016/193371 A1 | 12/2016 |

OTHER PUBLICATIONS

Litster et al., "Clinical efficacy and palatability of pradofloxacin 2.5% oral suspension for the treatment of bacterial lower urinary tract infections in cats", J. Vet Intern Med., 2007, pp. 990-995, vol. 5.

International Search Report for Application No. PCT/EP2018/053176, dated Apr. 26, 2018.

"Antioxidantien," Hunnius Pharmazeutisches Wörterbuch, 7th edition, (1993), Walter de Gruyter, Berlin, New York, pp. 111-113, with English translation.

*Primary Examiner* — Carlos A Azpuru
(74) *Attorney, Agent, or Firm* — McBee Moore & Vanik IP, LLC; Susan McBee

(57) ABSTRACT

The invention relates to pharmaceutical compositions in liquid form comprising pradofloxacin in an aqueous solution and citric acid or thioglycerol as antioxidants.

25 Claims, No Drawings

LIQUID COMPOSITION CONTAINING PRADOFLOXACIN

This application a Divisional Application of U.S. application Ser. No. 16/484,670, filed 8 Aug. 2019, which is a National Stage entry of International Application No. PCT/EP2018/053176, filed 8 Feb. 2018, which claims priority to European Patent Application No. 17155885.1, filed 13 Feb. 2017.

The invention relates to pharmaceutical compositions in liquid form comprising pradofloxacin in an aqueous solution and citric acid or thioglycerol as antioxidants.

DESCRIPTION OF RELATED ART

The chemical stability of solutions can be increased for example by using antioxidants. The oxidative degradation of a constituent can thereby be prevented. This is also customary in solutions for injection, where this is particularly the case. Pradofloxacin is generally known to be sensitive to oxidation.

Further, pradofloxacin has a tendency to precipitate from its solution. This process is sometimes very slow. It is therefore not easy and time consuming to determine whether a certain pradofloxacin solution is storage stable.

Such problems are sometimes avoided for example by choosing freeze-dried products instead which are reconstituted shortly before use. Freeze-dried products, however, are difficult to handle in practice and frequently only have a shelf life, of the reconstituted solution, of no more than 4 weeks after reconstitution, or must be discarded directly as the result of the possibility of particle formation. Accordingly, a ready-to-use solution is advantageous as solution for injection.

It is furthermore necessary that a suitable amount of the fluoroquinolone enters the serum after the administration, as this is also described in WO 99/29322. Again, this is not a matter of course with injectable fluoroquinolone compositions and may likewise depend on the animal species in question.

Also it is desirable to have compositions which allow for a high concentration of pradofloxacin. For a parenteral formulation to animals subcutaneous or intramuscular application is often preferred. Volumes for an s.c. or i.m. application cannot expand in volume and it is of advantage to inject volumes less than 10 ml per injection site. Thus concentrations of active ingredients like Pradofloxacin may have to be high (e.g. 10 to 30%).

Furthermore, it was found that liquid injectable pradofloxacin compositions can show discoloration which can be avoided by an antioxidant. It was further found that it is not easy to find suitable antioxidants which not only prevent the oxidation of pradofloxacin but also do not have any other unwanted effects.

SUMMARY

There have been found ready-to-use injectable compositions containing pradofloxacin which comprise sufficient concentration of the fluoroquinolone, which are stable and free from particle formation upon storage under pharmaceutical conditions, which in particular avoid oxidative degradation of pradofloxacin and maintain the color of the solution during storage, which are well tolerated and which have good serum kinetics.

The invention therefore relates to:
A liquid composition comprising:
(a) 1 to 30% (w/v) pradofloxacin
(b) 1 to 30% (w/v) of an acid
(c) 0.01 to 1% (w/v) of an antioxidant selected from citric acid and thioglycerol
(d) if appropriate, further pharmaceutical auxiliaries and/or additives
(e) and water as a solvent.

The invention further relates to the use of the aforementioned liquid compositions in the treatment of bacterial infections in animals.

The fluoroquinolone antibiotic pradofloxacin is described in WO 97/31001 as 8-cyano-1-cyclopropyl-7-((1S,6S)-2,8-diazabicyclo[4.3.0]nonan-8-yl)-6-fluoro-1,4-dihydro-4-oxo-3-quinolinecarboxylic acid (pradofloxacin), of the formula

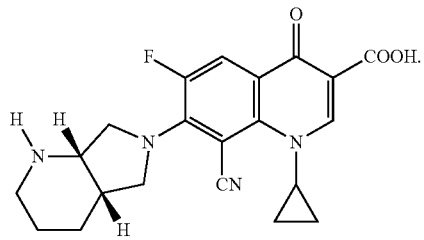 [SMILES: N#Cc1c(N2C[C@@H]3CCCN[C@@H]3C2)c(F)cc2c(=O)c(C(=O)O)cn(C3CC3)c12]

The term pradofloxacin includes its salts, hydrates and hydrates of the salts.

Optically active pradofloxacin can exist in the form of its racemates or in enantiomeric forms. Not only the pure enantiomers, but also their mixtures can be employed in accordance with the invention. Pradofloxacin that is usually used for pharmaceutical purposes is the isomer with the S,S-pyrrolidino-piperidine substituent.

Suitable salts are pharmaceutically useful acid addition salts and basic salts.

DETAILED DESCRIPTION OF A PREFERRED EMBODIMENT

Pharmaceutically useful salts are taken to mean, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. Furthermore, the compounds according to the invention can be bound to acidic or basic ion exchangers. Pharmaceutically useful basic salts which may be mentioned are the alkali metal salts, for example the sodium or potassium salts, the alkaline earth metal salts, for example the magnesium or calcium salts; the zinc salts, the silver salts and the guanidinium salts.

Hydrates are taken to mean not only the hydrates of the fluoroquinolone itself, but also the hydrates of its salts. A particular example which may be mentioned is the stable pradofloxacin trihydrate (see WO 2005/097789). According to a preferred embodiment pradofloxacin trihydrate is used in the preparation of the liquid compositions according to the present invention.

Pradofloxacin, being solid, can, under certain circumstances, form various crystal modifications; see, WO 00/31076 (crystal modification B), WO 00/31075 (crystal modification A), WO 00/52010 (crystal modification C), WO 00/52010 (crystal modification D), WO 00/31077 (semi hydrochloride). Among the crystal forms of the pradofloxacin anhydrate modification B is preferred.

The liquid compositions of the present invention contain pradofloxacin in a concentration of 3 to 30%, preferably 10 to 25%, more preferably 15 to 25%.

According to a further embodiment the liquid compositions of the present invention contain pradofloxacin in a concentration of 5 to 15%, preferably 10 to 15%. This further embodiment is preferred for animals with moderate body weight, e.g. animals which at the time of treatment have a body weight of up to approximately 100 kg. In the case of animals with a body weight of more than approximately 100 kg, the fluoroquinolone is typically employed in an amount of from 5 to 30%, preferably 10 to 25% and especially preferably 15 to 25%. Unless indicated otherwise the data in percentages are given, in each case, as w/v (i.e. in g/100 ml of solution) and—in case of salts or hydrates—are calculated to refer to the content of pure pradofloxacin.

The present compositions should be slightly to moderately acidic. Typically they have pH 5 or lower, preferably pH 2 to 4.8, more preferably pH 3 to 4.8.

In principle, a wide variety of acids can be used to adjust the pH of the present liquid compositions. However, it was found that some acids which are typically used in the art lead to non-desirable effects, in particular precipitation of the pradofloxacin. The following acids have been found to allow only low concentrations of active ingredient and are therefore not preferred for the present composition: aspartic acid, glutamic acid, citric acid, tartaric acid or hydrochloric acid.

Acids that can preferably be used according to the invention are: acetic acid, gluconic acid, gluconolactone, methanesulfonic acid, lactic acid, phosphoric acid or propionic acid. Gluconic acid or gluconolactone and methanesulfonic acid are particularly preferred. The concentration of the aforementioned acids in the present compositions is 1 to 30% (w/v), preferably 5 to 20% (w/v), more preferably 5 to 15% (w/v).

Gluconolactone means in particular the glucono delta-lactone. In the presence of water glucono delta-lactone is hydrolyzed to gluconic acid, with the balance between the lactone form and the acid form established as a chemical equilibrium. High concentrations of water, heat and high pH shift the equilibrium to the side of the gluconic acid.

To protect Pradofloxacin from oxidation an antioxidant is required. Without antioxidant the color of the yellow solution turns brownish or even brown, crystals occur and potentially degradation products form Pradofloxacin form. It was found that not many antioxidants are suitable to protect Pradofloxacin from oxidation, e.g. sodium disulfite, glutathione, tartaric acid or ascorbic acid are not suitable because they either cannot prevent discoloration, cause formation of particles or degradation products in the solution. The antioxidant in the present compositions is selected from citric acid and thioglycerol, citric acid is preferred. The preferred thioglycerol is 1-thioglycerol. The concentration of the antioxidant in the compositions is 0.01 to 1% (w/v), preferably 0.05 to 0.5% (w/v), more preferably 0.05 to 0.3% (w/v).

Other antioxidants were found to be less effective or even ineffective in the prevention of discoloration of the composition.

The liquid composition contains water as solvent. According to one embodiment water is the only solvent. According to a further embodiment water-miscible substances may be added as co-solvents, examples which may be mentioned are glycerol, propylene glycol, polyethylene glycols, tolerated alcohols such as ethanol, benzyl alcohol or n-butanol, ethyl lactate, ethyl acetate, triacetin, N-methylpyrrolidone, propylene carbonate, propylene glycol, glycofurol, dimethylacetamide, 2-pyrrolidone, dimethyl sulfoxide, isopropylidene glycerol, or glycerin formal. Preferred co-solvents are ethanol, benzyl alcohol or n-butanol. Mixtures of more than one co-solvent may also be used. Usually the co-solvents are present in concentrations of up to 50% preferably 1 to 30%, particularly preferably 5-20%

According to one embodiment of the invention the liquid composition may, besides water or water-miscible substances, also contain oils in the form of an emulsion as solvent. Among these, substances which may be mentioned are the vegetable, animal and synthetic oils such as cottonseed oil, sesame oil, soya oil, medium-chain triglycerides with a chain length of $C_{12}$-$C_{18}$, propylene glycol octanoate/decanoate or else paraffin.

In the present liquid compositions the solvent is usually employed at concentrations of from about 98 to 35%, 98 to 40% or 98 to 45%, preferably of from about 90 to 60% or in an alternative preferred embodiment of from about 95 to 75%, or especially preferably at 80 to 60% or in an alternative especially preferred embodiment at 94 to 80%. The data in percentages are given, in each case, as w/v.

The liquid composition may contain preservatives, for example aliphatic alcohols such as benzyl alcohol, ethanol, n-butanol, phenol, cresols, chlorobutanol, para-hydroxybenzoic esters (in particular the methyl and propyl esters), salts or the free acids of the carboxylic acids, such as sorbic acid, benzoic acid, lactic acid or propionic acid, benzalkonium chloride, benzethonium chloride or cetylpyridinium chloride. Typical concentrations (known to the skilled person) used in the pharmaceutical area are generally range from 0.01 to 30% (w/v). For ethanol the preferred concentration is 10 to 30% (w/v), particularly preferably 15 to 25% (w/v). For butanol, the preferred concentration is 0.1 to 10% w/v preferably 1 to 5% (w/v). for preservatives other than ethanol or butanol the preferred concentration range is from 0.01 to 5% (w/v).

Depending on the type of formulation and on the form of administration, the pharmaceutical compositions according to the invention may contain further customary, pharmaceutically acceptable additives and adjuvants. Examples which may be mentioned are:

Emulsifiers, in particular for emulsions, such as, for example, Tween80 (Polysorbate 80), CremophorEL (polyethoxylated castor oil), Solutol HS15 (Macrogol 15 Hydroxystearate) or Poloxamer188 (Poloxamer is the international non-proprietary name for block copolymers of ethylene oxide and methyloxirane). Iso-osmotics, such as, for example, sodium chloride, glucose or glycerol.

In addition to the fluoroquinolones, the compositions according to the invention may comprise further pharmaceutical active ingredients. For example, the fluoroquinolones may also be employed in combination with, for example, pain killers, in particular what are known as NSAIDs (nonsteroidal antiinflammatory substances). Such NSAIDs may be, for example: meloxicam, flunixin, ketoprofen, carprofen, metamizole or (acetyl)salicylic acid.

The pharmaceuticals according to the invention can be prepared by dissolving the ingredients in the aqueous phase. Preferably, the acid is dissolved in water first, then the antioxidant and then pradofloxacin and—if applicable—other ingredients are added to form a solution. Alternatively the antioxidant is dissolved in water first and then Pradofloxacin and if applicable—other ingredients are either added after or together with Pradofloxacin to form a solution. Another way of preparation is to add all ingredients to the aqueous phase at once and to dissolve them all in one step.

To ensure best protection for Pradofloxacin against oxidation manufacturing can be conducted under inert gas conditions, e.g. nitrogen or argon aeration can be applied during manufacturing of the solution. Preferably an inert gas such as argon or nitrogen is applied to the aqueous phase before adding Pradofloxacin.

The solution is sterilized e.g. by filtration. The composition may then be filled in appropriate primary packaging containers. Optionally, one or more steps of this process may be done under inert gas atmosphere, e.g. using nitrogen.

The liquid compositions according to the present invention show a very good chemical and physical stability even at elevated temperatures up to 40° C.

In general, the pharmaceutical preparations according to the invention are suitable for use in humans and animals. They are preferably employed in animal keeping and animal husbandry in livestock, breeding animals, zoo animals, laboratory animals, experimental animals and pets.

The livestock and breeding animals include mammals such as, for example, cattle, horses, sheep, pigs, goats, camels, water buffalos, donkeys, rabbits, fallow deer, reindeer, fur bearers such as, for example, minks, chinchilla, racoons and birds such as, for example, chickens, geese, turkeys, ducks, pigeons and bird species for keeping on domestic premises and in zoos.

The laboratory and experimental animals include mice, rats, guinea pigs, golden hamsters, dogs and cats.

The pets include rabbits, hamsters, guinea pigs, mice, horses, reptiles, suitable bird species, dogs and cats.

According to one embodiment the liquid compositions according to the invention can be employed in pets, preferably they can be used in cats or dogs.

According to a preferred embodiment the present compositions are employed in livestock such as cattle, sheep, pig, goat, horses and buffalo. Especially preferred livestock is cattle and swine.

Thus, according to one particularly preferred embodiment the present compositions are employed in cattle.

According to a further particularly preferred embodiment the present compositions are employed in swine.

The administration can be effected prophylactically or else therapeutically In principle the compositions described herein can be administered to the target organism via different routes. However preferably, they can be administered parenterally, in particular by means of an injection (for example subcutaneously, intramuscularly, intravenously, intramammarially, intraperitoneally). Subcutaneous or intramuscular injection is preferred.

Typical dosages are in the range of about 5 to 20 mg/kg target animal. With regard to the treatment scheme one application may be sufficient but application on two or more days may be required depending on the circumstances and the disease. Usually the application is on consecutive days.

The pharmaceuticals according to the invention are distinguished by good solubility of the active substance and good chemical and physical stability at pharmaceutically relevant storage conditions. Moreover, they have good tolerance and suitable serum kinetics in animals, in particular upon parenteral administration.

EXAMPLES

Percentages in all examples are given as % (w/v). In all examples the pH value is adjusted to a pH of 4.4 to 4.8 with the required amounts of the acid (indicated as "q.s.")

Example 1

| | |
|---|---|
| 20% | Pradofloxacin (used as 22.73% Pradofloxacin trihydrate) |
| q.s. (7 to 13%) | gluconolactone |
| 0.1% | citric acid |
| Ad 100% | water |

Example 2

| | |
|---|---|
| 20% | Pradofloxacin (used as 22.73% Pradofloxacin trihydrate) |
| q.s. (7 to 13%) | gluconolactone |
| 0.3% | citric acid |
| Ad 100% | water |

Example 3

| | |
|---|---|
| 10% | Pradofloxacin (used as 22.73% Pradofloxacin trihydrate) |
| q.s. (4 to 8%) | gluconolactone |
| 0.1% | citric acid |
| Ad 100% | water |

Example 4

| | |
|---|---|
| 5% | Pradofloxacin (used as 22.73% Pradofloxacin trihydrate) |
| q.s. (1 to 5%) | gluconolactone |
| 0.1% | citric acid |
| Ad 100% | water |

Example 5

| | |
|---|---|
| 20% | Pradofloxacin (used as 22.73% Pradofloxacin trihydrate) |
| q.s. (7 to 13%) | gluconolactone |
| 0.1% | thioglycerol |
| Ad 100% | water |

Example 6

| | |
|---|---|
| 20% | Pradofloxacin (used as 22.73% Pradofloxacin trihydrate) |
| q.s. (7 to 13%) | gluconolactone |
| 0.3% | thioglycerol |
| Ad 100% | water |

Example 7

| | |
|---|---|
| 20% | Pradofloxacin (used as 22.73% Pradofloxacin trihydrate) |
| q.s. (7 to 13%) | gluconolactone |
| 0.1% | citric acid |
| 0.1% | thioglycerol Ad 100% water |

Example 8

| | |
|---|---|
| 20% | Pradofloxacin (used as 22.73% Pradofloxacin trihydrate) |
| q.s. (3 to 5%) | methanesulfonic acid |
| 0.1% | citric acid |
| Ad 100% | water |

Example 9

| | |
|---|---|
| 15% | Pradofloxacin (used as 22.73% Pradofloxacin trihydrate) |
| q.s. (2 to 4%) | methanesulfonic acid |
| 0.1% | citric acid |
| Ad 100% | water |

Example 10

| | |
|---|---|
| 5% | Pradofloxacin (used as 22.73% Pradofloxacin trihydrate) |
| q.s. (0.5 to 2%) | methanesulfonic acid |
| 0.1% | citric acid |
| Ad 100% | water |

Stability Tests:
1. Color:

Formulations we placed in storage at different temperatures. The color of each solution was observed visually and photographs we taken for documentation:

TABLE 1

Results after 10 months storage at 25° C. or 6 months storage at 40° C.

| Yellow solution with no or minimal color changes: | Yellow solution with significant, not acceptable color changes: | Yellow solution with not acceptable particle formation: | Yellow solution with not acceptable formation of by-products: |
|---|---|---|---|
| Exs. 1, 2 (citric acid), Exs. 5, 6 (thioglycerol) | Similar compositions* with ascorbic acid, sodium ascorbate, EDTA, glutathione | Similar compositions* with tartaric acid | Similar composition* with sodium disulfite |

*Similar compositions had 0.05, 0.1 or 0.15% (w/v) of the respective antioxidant 2. Storage Stability (HPLQ):

Formulations with citric acid or thioglycerol as antioxidants were manufactured, placed in storage at elevated temperature and analyzed by HPLC (content of pradofloxacin and side-products).

TABLE 2

Results for example 1 (0.1% citric acid)

| Parameter | Start | 4 weeks | 8 weeks |
|---|---|---|---|
| storage temperature | | 40° C. | 40° C. |
| assay citric acid | 0.10 | 0.10 | 0.10 |
| assay Prado % [w/v] | 20.3 | — | 19.7 |
| NK1 - unspec., RT1.3 [%] | | — | 0.20 |
| NK2 - unspec., RT1.65 [%] | | — | <0.01 |
| NK3 - unspec., RT2.17 [%] | | — | 0.13 |
| NK4 - unspec., RT2.39 [%] | | — | — |
| NK* - unspec., RT2.55 [%] | | — | — |
| color [visual] | yellow | yellow | yellow |
| color [Ph. Eur.] | GY1 | GY1 | GY1 |

NK = unspecified impurity (% relative to a.i.); RT = retention time (min.)

Formulations manufactured according to example 1 remain stable with regard to the content for citric acid and pradofloxacin. The changes in the pradofloxacin concentration after 8 weeks are within the tolerance of the analytical method, the concentration after 8 weeks is well within the intended specification. However, impurities at a low level can be found at 40° C. after 8 weeks. The formulation stored at 40° C. remains yellow, the color does not change (no discoloration), showing the suitability of the chosen antioxidant.

TABLE 5

Results for example 5 (0.1% thioglycerol)

| Parameter | Start | 4 weeks | 8 weeks |
|---|---|---|---|
| storage temperature | | 40° C. | 40° C. |
| assay thioglycerol 1% [w/v] | 0.10 | 0.05 | 0.02 |
| assay thioglycerol 2% [w/v] | 0.01 | 0.05 | 0.08 |
| sum thioglycerol 1 + 2% [w/v] | 0.11 | 0.10 | 0.09 |
| assay Prado % [w/v] | 20.4 | — | 19.8 |
| NK1 - unspec., RT1.3 [%] | | — | 0.20 |
| NK2 - unspec., RT1.65 [%] | | — | <0.01 |
| NK3 - unspec., RT2.17 [%] | | — | 0.12 |

TABLE 5-continued

Results for example 5 (0.1% thioglycerol)

| Parameter | Start | 4 weeks | 8 weeks |
|---|---|---|---|
| NK4 - unspec., RT2.39 [%] | | — | — |
| NK* - unspec., RT2.55 [%] | | — | 0.06 |
| color [visual] | yellow | yellow | yellow |
| color [Ph. Eur.] | GY1 | >GY1 | GY1 |

NK = unspecified impurity (% relative to a.i.); RT = retention time (min.) "thioglycerol 2" = oxidation product of thioglycerol Formulations manufactured according to example 5 remain stable with regard to the content of Pradofloxacin but show a decrease for thioglycerol 1 from 0.1% to 0.02% as expected for the antioxidant. Impurities at low levels can be found at 40° C. after 8 weeks. The formulation stored at 40° C. remains yellow, the color does not change (no discoloration), showing the suitability of the chosen antioxidant.

The invention claimed is:

1. A method of treating a bacterial infection in an animal comprising administering to the animal a liquid composition comprising:
   (a) 1 to 30% (w/v) pradofloxacin;
   (b) 1 to 30% (w/v) of an acid;
   (c) 0.01 to 1% (w/v) of an antioxidant selected from the group consisting of citric acid and thioglycerol;
   (d) optionally, one or more pharmaceutical auxiliaries and/or additives and;
   (e) water as a solvent.

2. The method according to claim 1, wherein the antioxidant is present in a concentration of from 0.05 to 0.5% (w/v).

3. The method according to claim 2, wherein the antioxidant is present in a concentration of from 0.05 to 0.3% (w/v).

4. The method according to claim 1, wherein the acid is selected from the group consisting of: gluconic acid, gluconolactone, methanesulfonic acid, lactic acid, and propionic acid.

5. The method according to claim 4, wherein the acid is selected from the group consisting of gluconic acid or gluconolactone.

6. The method according to claim 1 which is a solution.

7. The method according to claim 1 which has a pH of from 2 to 5.

8. The method according to claim 1, wherein the antioxidant is citric acid.

9. The method according to claim 8, wherein the antioxidant is present in a concentration of from 0.05 to 0.5% (w/v).

10. The method according to claim 9, wherein the antioxidant is present in a concentration of from 0.05 to 0.3% (w/v).

11. The method according to claim 8, wherein the acid is selected from the group consisting of: gluconic acid, gluconolactone, methanesulfonic acid, lactic acid, and propionic acid.

12. The method according to claim 11, wherein the acid is selected from the group consisting of gluconic acid or gluconolactone.

13. The method according to claim 8, which is a solution.

14. The method according to claim 8, which has a pH of from 2 to 5.

15. The method according to claim 1, wherein the antioxidant is thioglycerol.

16. The method according to claim 15, wherein the antioxidant is present in a concentration of from 0.05 to 0.5% (w/v).

17. The method according to claim 16, wherein the antioxidant is present in a concentration of from 0.05 to 0.3% (w/v).

18. The method according to claim 15, wherein the acid is selected from the group consisting of: gluconic acid, gluconolactone, methanesulfonic acid, lactic acid, and propionic acid.

19. The method according to claim 18, wherein the acid is selected from the group consisting of gluconic acid or gluconolactone.

20. The method according to claim 15, which is a solution.

21. The method according to claim 15, which has a pH of from 2 to 5.

22. The method according to claim 1, wherein the composition is administered in a dose of 5 to 20 mg/kg pradofloxacin.

23. The method according to claim 22, wherein the animal is a dog or a cat.

24. The method according to claim 1, wherein the composition is administered parenterally.

25. The method according to claim 24, wherein the composition is administered subcutaneously or intramuscularly.

* * * * *